(12) United States Patent
Jahan et al.

(10) Patent No.: US 9,387,198 B1
(45) Date of Patent: Jul. 12, 2016

(54) INHIBITORS OF ADVANCED GLYCATION END-PRODUCTS (AGES)FORMATION

(71) Applicants: Humera Jahan, Karachi (PK); Muhammad Iqbal Choudhary, Karachi (PK); Zarbad Shah, Karachi (PK); Khalid M. Khan, Karachi (PK); Atta-ur Rahman, Karachi (PK)

(72) Inventors: Humera Jahan, Karachi (PK); Muhammad Iqbal Choudhary, Karachi (PK); Zarbad Shah, Karachi (PK); Khalid M. Khan, Karachi (PK); Atta-ur Rahman, Karachi (PK)

( * ) Notice: Subject to any disclaimer, the term of this patent is extended or adjusted under 35 U.S.C. 154(b) by 0 days.

(21) Appl. No.: 14/634,045

(22) Filed: Feb. 27, 2015

(51) Int. Cl.
 *A01N 43/52* (2006.01)
 *A61K 31/415* (2006.01)
 *C07D 235/00* (2006.01)
 *A61K 31/4184* (2006.01)

(52) U.S. Cl.
 CPC ................................ *A61K 31/4184* (2013.01)

(58) Field of Classification Search
 None
 See application file for complete search history.

*Primary Examiner* — Jeffrey H Murray
(74) *Attorney, Agent, or Firm* — Sarfaraz K. Niazi

(57) ABSTRACT

The invention relates to methods of inhibiting the protein glycation process and the associated formation of Advanced Glycation End products (AGEs) in hyperglycemia by administering 6-Nitrobenzimidazole derivatives. These derivatives were found to be effective not merely against the formation of AGE, but they can inhibit the action of AGEs at post-receptor levels.

3 Claims, 3 Drawing Sheets

1  2  3

4  5

6  7

8  9

10

INHIBITORS OF ADVANCED GLYCATION END-PRODUCTS (AGES) FORMATION

BACKGROUND OF THE INVENTION

The accelerated non-enzymatic modifications of amino groups of proteins (short- and long-lived), lipids, and nucleic acids by reducing sugars, such as glucose and fructose, play a critical role in the pathogenesis of multiple diseases. These include diabetes mellitus, atherosclerosis Alzheimer's diseases, inflammatory arthritis, osteoarthritis, vascular stiffening, and cataract (Ishibashi Y, et al., 2013; Kroner Z, 2009; Reddy V P, et al., 2006).

The non-enzymatic glycation reaction is also called the Maillard reaction, characterized by a French scientist, Louis Camille Maillard; in 1912 (Reddy V P, et al., 2006). The Maillard reaction is comprised of multiple series of non-enzymatic reactions. In its initial phase, sugars react non-enzymatically with amino groups forming Schiff bases, which subsequently rearrange to form ketoamine or Amadori products. The Amadori product may undergo glycoxidation reaction in the presences of reactive oxygen species (ROS) and reactive nitrogen species (RNS) to form highly reactive dicarbonyl compounds. These include 3-deoxyglucosone, glyoxal, and methylglyoxal. These dicarbonyl compounds react relatively faster with amino groups of proteins, phospholipids, and nucleic acids, and hence result in the formation of a multitude of heterogonous end products, known as advanced glycation end products (AGEs) (Reddy V P, et al., 2002).

Advanced glycation end products (AGEs) formation is a slow process; therefore, AGEs accumulation is predominant on long-lived proteins, including collagens and lens crystallins under physiological milieu (Reddy V P, et al., 2006). This leads to the alteration of biological proteins functions by intra- and inter-molecular cross-links. In addition to this, AGEs form complexes with metal ions, such as $Cu+$ and $Fe++$, and hence further accelerate the formation of reactive oxygen and nitrogen species. It has been recognized that diabetes mellitus, which is characterized by hyperglycemia, is a pivotal source of AGEs in human body (Wu C H, et al., 2011; Reddy V P, et al., 2006). It has been stated that hyperglycemic environment increases the formation of AGEs, therefore, AGEs accumulation is several fold higher in diabetic individuals than normal individuals (Ahmed K A, et al., 2009). In addition to their endogenous formation, other sources of these heterogonous moieties in the human body are AGEs-enriched diet, and smoking (Wu C H, et al., 2011; Reddy V P, et al., 2006).

Several AGEs receptors, referred to as receptors for advanced glycation end products (RAGE), involve in signal transduction mechanisms. RAGE a remembers of cell surface immunoglobulin superfamily and are expressed by multiple cell types, including endothelial cells, smooth muscle cells, macrophages, and platelets. They perturb cellular functions, such as formation of intracellular generation of reactive oxygen species, followed by their recognition and interaction with AGEs. In diabetic patients, accumulation of AGEs ligands causes enhanced expressions of RAGE in vasculatures (Goldin A, et al., 2006). The AGE-RAGE interaction plays a pivotal role in the development of chronic complications, such as cardiovascular complications, nephropathy, neuropathy, and retinopathy (Reddy V P, et al., 2006).

Early attention was focused on aminoguanidine, an inhibitor of AGEs formation which sequesters reactive dicarbonyl compounds formed during the Maillard reaction. It also attenuates the oxidative stress, such as trapping of reactive nitrogen species and chelation of transition metal-ions. Although it involves in suppression of AGEs formation through combination of all these mechanisms, the drug was withdrawn from phase III clinical trials because of undesirable side effects (Adisakwattana S, et al., 2012; Reddy V P, et al., 2006). These involve flu-like symptoms, gastrointestinal disorders, deficiency of Vit-B6, and elevated levels of homocysteine (Adisakwattana S, et al., 2012; Gutierrez R M P, et al., 2010; Reddy V P, et al., 2006).

BRIEF SUMMARY OF THE INVENTION

In view of AGEs-mediated extra- and intra-cellular derangements and the associated oxidative stress, much attention has been focused to develop and identify safe and effective advanced glycation end products (AGEs) inhibitors for the treatment of diabetes-associated complications, end-stage renal diseases. This therapeutic approach would be beneficial in preventing and delaying the AGEs-associated late complications of diabetes.

We identified the anti-glycation potential of 6-nitrobenzimidazole derivatives (1-10). Nitrobenzimidazole important pharmacophore in the field of drug discovery. Various benzimidazoles are in clinical use. These include flubendazole and thiabendazole, lansoprezole and omeprazole, and astemizole for the treatment of anthelmintic, antiulcerative, and antihistaminic, respectively (Gurvinder S, et al., 2013). The anti-glycation activity of these derivatives was explored by high-throughput screening method, using fluorescence-based anti-glycation assay (see Table-1). Cytotoxicity evaluation was also carried out against mouse fibroblast (3T3) cell-line by employing MTT-assay. The in-vitro cellular-based mechanistic approaches were also employed to study the effectsof 6-nitrobenzimidazole derivativeson fructose-derived AGE-induced intracellular reactive oxygen species (ROS) production, and associated diminished growth of the hepatocytes (rat hepatocytes, CC1-cell line) via dichlorofluorescin diacetate (DCFH-DA) technique and MTT assay, respectively. Besides their anti-glycation activity, these derivatives were found to be nontoxic and reduced the fructose-derived AGE-mediated intracellular ROS production and impaired proliferation of the hepatocytes.

TABLE 1

In Vitro Anti-glycation Activity and Cytotoxicity of 6-Nitrobenzimidazoles (1-10).

| Compound | Anti-glycation Activity | | Cytotoxicity |
|---|---|---|---|
| | % Inhibition | $IC_{50} \pm SEM$ [μM] | % Inhibition |
| 3-(6-Nitro-1H-benzimidazol-2-yl)-1,2-benzenediol (1) | 88.8% | 17.7 ± 0.001 | 35.9% |
| 2-(6-Nitro-1H-benzimidazol-2-yl)-1,4-benzenediol (2) | 88.2% | 48.7 ± 0.006 | 21.1% |
| 6-Nitro-2-(3-thienyl)-1H-benzimidazole (3) | 81.9% | 142 ± 0.014 | 19.7% |
| 4-(6-Nitro-1H-benzimidazol-2-yl)-1,2,3-benzenetriol (4) | 91.2% | 71.7 ± 0.008 | 9.8% |
| 2-(6-Nitro-1H-benzimidazol-2-yl)-1,3,5-benzenetriol (5) | 89.2% | 109 ± 0.02 | 4.0% |
| 4-(6-Nitro-1H-benzimidazol-2-yl)-1,2-benzenediol (6) | 86.0% | 25.5 ± 0.000 | 3.4% |
| 4-(6-Nitro-1H-benzimidazol-2-yl)-1,3-benzenediol (7) | 87.8% | 52.4 ± 0.001 | 37.4% |
| 2-(4-Methylphenyl)-6-nitro-1H-benzimidazole (8) | 70.8% | 192 ± 0.017 | 59.2% |
| 6-Nitro-2-(4-nitrophenyl)-1H-benzimidazole (9) | 61.7% | 114 ± 0.005 | 45.2% |

TABLE 1-continued

In Vitro Anti-glycation Activity and Cytotoxicity of 6-Nitrobenzimidazoles (1-10).

| Compound | Anti-glycation Activity | | Cytotoxicity |
|---|---|---|---|
| | % Inhibition | $IC_{50} \pm$ SEM [μM] | % Inhibition |
| 4-(6-Nitro-1H-benzimidazol-2-yl) phenol (10) | 76.9% | 194 ± 0.039 | 3.6% |

DETAILED DESCRIPTION OF THE INVENTION

Figure 1:
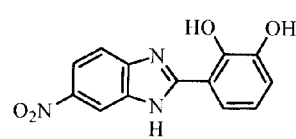
FIG. 1 depicts the structures of 6-nitrobenzimidazole derivatives, novel identified anti-glycation agents.
Figure 1:
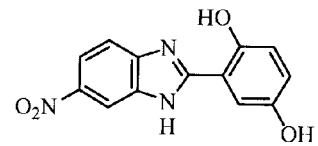
Figure 1:
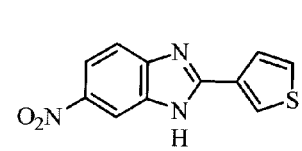
Figure 1:
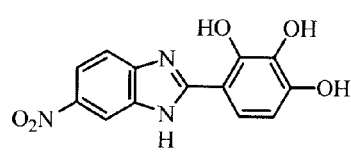
Figure 1:
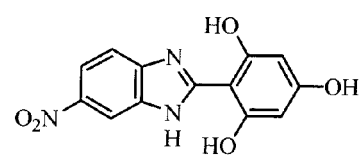
Figure 1:
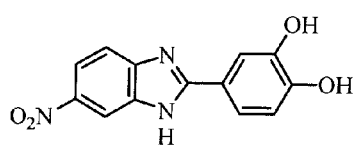
Figure 1:
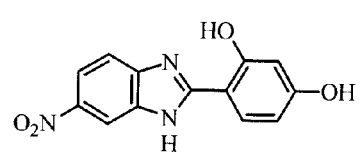
Figure 1:
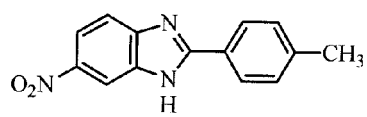
Figure 1:
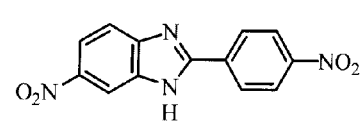
Figure 1:
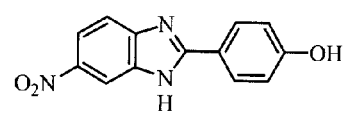
Figure 2A:
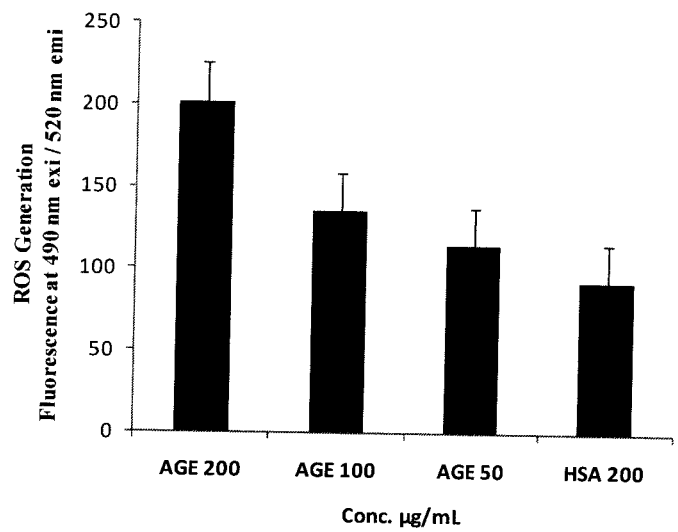
FIG. 2A depicts the AGE induced ROS generation in the hepatocytes (CC1-Cell line). The cells were first treated with DCFH-DA and then incubated with 200 μg/mL of AGEs at 37° C. for 24 hours. The specified ROS values are the mean of two independently performed experiments.
Figure 2B:
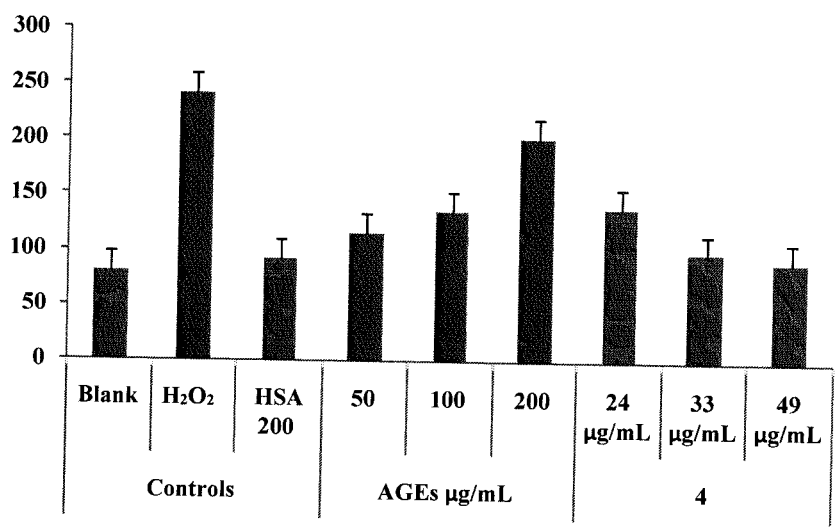
FIG. 2B depicts the effect of compound 4, novel identified anti-glycation agent of 6-nitrobenzimidazole derivatives, on fructose-derived AGEs induced ROS formation in the hepatocytes. The cells were initially treated with DCFH-DA at 37° C. for 45 mins and then with the compound 4 at various concentrations, and co-incubated with 200 μg/mL of AGEs at 37° C. for 24 hours. The specified ROS values are the mean of two independently performed experiments.
Figure 3:
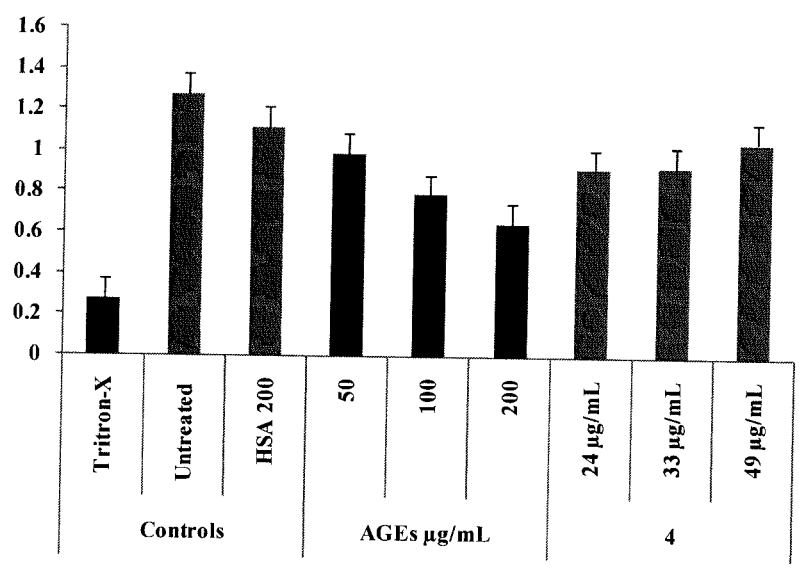
FIG. 3 depicts the effect of compound 4, novel identified anti-glycation agent of 6-nitrobenzimidazole derivatives, on the hepatocytes growth and proliferation, co-incubated with the 200 μg/mL AGEs. The cells were treated with various concentrations of compound 4 at 37° C. for 24 hours. The specified absorbance is the mean of two independently performed experiments.

The current invention is related to the discovery of novel compounds which can inhibit protein glycation process and the associated AGEs formation in hyperglycemia.

Example 1

Glycation of Human Serum Albumin (HSA)

Chemicals: Rutin monohydrate and human serum albumin (HSA, Essential fatty acids free) were purchased from Sigma Aldrich, St. Louis, Mo., USA. Sodium azide (NaN3), dimethyl sulfoxide (DMSO), and D-fructose were obtained from Merck, Darmstadt, Germany. The solutions were prepared under sterile conditions using deionized water at 25° C.

Procedure of the Assay: The glycated HSA was prepared in accordance with a minor modification of the Sattarahmady method (Sattarahmady N., et al., 2007). In brief, HSA (10 mg/mL) was incubated with a supra-physiological concentration (500 mM) of D-fructose to foster the reaction in a 100 mM sodium phosphate buffer (NaHPO4/NaH2PO4), containing 0.1 mM sodium azide ($NaN_3$) under dark and, sterile environment at 37° C. for seven days. Prior to incubation, rutin (reference compound) and 6-nitrobenzimidazole derivatives were added to a reaction mixture to a final concentration of 1 mM. DMSO was used as a solvent (final concentration: 10%) in this assay.

Glycated HSA Detection by Fluorescence Intensity: The glycated HSA formation was measured by AGE-specific fluorescence intensity at 340 nm (an excitation wavelength) and 440 nm (an emission wavelength) using Spectra Max Spectrophotometer (Applied Biosystems, CA, USA).

Estimation of Glycated HSA Percentage Inhibition: The following formula was employed to estimate the percent fluorescence inhibition of glycated HSA.

Percentage Inhibition=(1−Fluorescence of test compounds/Fluorescence of glycated-HSA)×100

Where,

Test compounds=6-Nitrobenzimidazole derivatives

IC50 Value Determination: 6-Nitrobenzimidazole derivatives, which showed moderate to excellent anti-glycation activity, were further tested for their IC50 values by EZ-Fit software.

Results: 6-Nitrobenzimidazole derivatives 1, 2, 4, 6, and 7 exhibited significant anti-glycation activity, with lower $IC_{50}$ values as compared to the reference compound, rutin (IC50=70±0.5 μM). Compounds 3, 5, and 8-10 showed a moderate anti-glycation activity, as presented in Table-1.

Discussion: The preliminary findings from the structure-activity relationship (SAR) studies established that the presence of hydroxyl moieties, either away or vicinal to each other on phenyl rings of 6-nitrobenzimidazole derivatives is essential for the anti-glycation activity.

Example 2

6-Nitrobenzimidazole Derivatives Inhibitors of Fructose-Derived AGE-Mediated Intracellular Generation of Reactive Oxygen Species (ROS)

Chemicals: Dichlorofluorescindiacetate (DCFH-DA) probe, hydrogen peroxide ($H_2O_2$), dimethyl sulfoxide (DMSO; tissue culture grade) and phosphate buffer saline (PBS) were acquired from Sigma, St. Louis, Mo., USA. Black fluorescence 96-well plates (Tissue culture treated) were obtained from Thermo Fisher Scientific, Waltham, Mass., USA.

Procedure of the Assay: Briefly, 6×104 cells/mL cells (normal rat hepatocytes: CC1-Cell line) were seeded on a 96-well plate and kept for 24 hours in an incubator, containing 5% $CO_2$ at 37° C. Before treating with fructose-derived AGEs, the cells were exposed to serum free MEM (minimum essential medium) for next 24 hours. Initially the cells were incubated with 10 μM DCFH-DA non fluorescent probe, for 45 mins in the dark environment. At the end of the incubation, the cells were washed with 1×PBS twice and were incubated with varying concentrations of the fructose-derived AGE, such as 0, 50, 100, and 200 μg/mL, to investigate the AGEs effect on the production of intracellular ROS in a dose dependent manner. In the next step, the cells were incubated with the different concentrations (24, 33, and 49 μM) of 6-nitrobenzimidazole derivatives, in the presence of AGEs (200 μg/mL) at 37° C. for 24 hours. The control was treated with 0.5% $H_2O2$ just before 1 hour prior to halt the incubation period.

Detection of Fluorescence Intensity: The intensity of fluorescence was measured at an excitation 490 nm and an emission 520 nm, using Spectra Max Spectrophotometer (Applied Biosystems, CA, USA).

Estimation of Percentage Inhibition: The inhibition of AGEs-induced intracellular production of ROS in rat hepatocytes incubated with novel anti-glycation agents, 6-nitrobenzimidazole derivatives, was measured by the following formula:

Percentage Inhibition=100−[(Fluorescence of test compound−Fluorescence of blank)/(Fluorescence of control−Fluorescence of blank)×100]

Where,
Blank=Normal rat hepatocytes
Control=Rat hepatocytes treated with 0.5% 11202
Test compound=6-Nitrobenzimidazole derivative Results: The effect of fructose-derived AGEs on ROS formation was initially determined at different concentrations, such as 50, 100 and 200 µg/mL, using cell permeable non-fluorescent probe, DCFHDA. The probe becomes impermeable following the cleavage by estrases and emits green fluorescence upon oxidation in the presence of intracellular ROS. The increased green fluorescence intensity was observed as the concentration of the AGEs increases, which is associated with the increased production of ROS, as depicted in Table-2.

TABLE 2

Effect of Fructose-derived AGEs on the
Intracellular ROS Production.

| AGEs Concentration | Fluorescence (Average) |
|---|---|
| 200 µg/mL | 201.9 |
| 100 µg/mL | 135.3 |
| 50 µg/mL | 114.4 |
| HSA 200 µg/mL | 92.3 |

To investigate the anti-glycation effect of 6-nitrobenzimidazole derivatives at the cellular level, the derivatives were selected on the basis of their anti-glycation activity and low cytotoxicity.

Effect of 6-nitrobenzimidazole derivative (24 µM) on the hepatocytes ROS production, co-incubated with fructose-derived AGEs. Initially, the anti-glycation effect of compound 4, belonging to 6-nitrobenzimidazoles, was determined at 24 µM concentration. Compound 4 exhibited moderate activity against ROS production, particularly peroxynitrite (NOO·) and hydrogen peroxide ($H_2O_2$), co-incubated with AGE (200 µg/mL), as shown in Table-3.

TABLE 3

Effect of 6-Nitrobenzimidazole Derivative on
AGE-mediated Intracellular ROS Production.

| Compound 4 Conc. µM | Fluorescence (Average) | Percentage Inhibition |
|---|---|---|
| 24 µM | 138.8 | 63.6% |
| 33 µM | 97.5 | 89.2% |
| 49 µM | 90.7 | 93.4% |

Effect of 6-nitrobenzimidazole derivative (33 µM) on the hepatocytes ROS production, co-incubated with fructose-derived AGEs. The effect of compound 4 on ROS production at 33 JAM concentration, co-incubated with fructose-derived AGE (200 µg/mL), was evaluated. Compound 4 significantly impaired the ROS production in response to AGEs in rat hepatocytes, as shown in Table-3.

Effect of 6-nitrobenzimidazole derivative (49 µM) on the hepatocytes ROS production, co-incubated with fructose-derived AGEs. The effect of compound 4 at 49 µM concentration against the ROS production, co-incubated with fructose-derived AGE (200 µg/mL), was also evaluated. Compound 4 inhibited the AGE-induced ROS production in rat hepatocytes in a remarkably significant manner, as shown in Table-3.

Discussion: The current study revealed the anti-glycation effect of 6-nitrobenzimidazole derivatives at the post-receptor level. The derivative exhibited the anti-glycation effect in a concentration dependant manner. Compound 4 inhibited the interaction of AGEs with RAGE (receptors for advanced glycation end products), and hence impaired the production of the intracellular ROS. RAGE expressions are up-regulated in hyperglycemic environment and play a critical role in the pathogenesis of late complications of diabetes (Barlovic D P, et al., 2011). Therefore, AGE-RAGE nexus is a novel therapeutic approach for preventing and delaying the diabetes associated chronic complications. Newly identified novel compound 4 was found significantly effective in this regard, and hence provide novel therapeutic modality for the prevention of chronic diabetic complications.

Example 3

6-Nitrobenzimidazole Derivatives Inhibitors of
Fructose-Derived AGE-Mediated Diminished
Growth of the Hepatocytes Chemicals: Minimum Essential Medium (MEM) with L-glutamine, sodium bicarbonate, trypsin-EDTA, and penicillin-streptomycin were purchased from Sigma, St. Louis, Mo., USA. Sterile, tissue culture treated, round bottom 96-well plates were obtained from Thermo Fisher Scientific, Waltham, Mass., USA. CC1— Cell line (Normal, rat hepatocytes) was obtained from ATCC, Manassas, Va., USA.

Procedure of the Assay: Briefly, $5 \times 10^4$ cells/mL (CC1-Cell line: rat hepatocytes) were seeded on a 96-well plate and were initially co-incubated with various concentrations of the AGEs (such as 0, 50, 100, and 200 µg/mL). Fructose-derived AGEs were prepared by mixing 20 mg/mL HSA (Human serum albumin) with 500 mM fructose solution, containing 200 U/mL penicillin, 200 µg/mL streptomycin and 80 µg/mL gentamycin in a 100 mM sodium phosphate buffer. The mixture was incubated at 37° C. for 12 weeks under dark sterile environment. The cells were then incubated with the test compound at different concentrations, such as 24, 33, and 49 µM, co-incubated with 200 µg/mL fructose-derived AGEs in an incubator containing 5% $CO_2$ at 37° C. for 24 hours. The cells treated with Triton X-100 were used as a blank, while normal cells remain untreated were used as a control. All the treatment with the test compound and the AGEs were completed in serum free medium (SFM).

MTT Assay: Following 24 hours of incubation, the plate was decanted to remove the medium and the cells were washed with 1×PBS. The MTT-dye (50 µL: 2 mg/mL) was then loaded to each well. 200 µL (final reaction volume) was reconstituted by serum free-MEM (Minimum essential media) in a dark environment. The plate was incubated in 5% $CO_2$ containing incubator at 37° C. for the next 4 hours. At the end of the incubation, the medium was removed and the crystals were dissolved by adding 100 µL DMSO into each well.

Measurement of Absorbance: The intensity of purple colored solution was measured at the wavelength of 540 nm, using Spectra Max Spectrophotometer (Applied Biosystems, CA, USA).

Percentage Inhibition: The inhibition of fructose-derived AGEs-induced impaired growth of the hepatocytes, co-incubated with the test compound, was determined by the following formula:

Percentage inhibition=100−[(Test compound absorbance−BlankAbsorbance)/(Control absorbance−Blank Absorbance)×100]

Where,
Blank=Triton X-100 treated rat hepatocytes

Control=Normal rat hepatocytes
Test Compound=6-nitrobenzimidazole derivatives

Results: The effect of fructose-derived AGEs using various concentrations, such as 50, 100 and 200 μg/mL, was investigated on hepatocytes growth and proliferation, as presented in Table-4. The 200 μg/mL concentration of fructose-derived AGEs had completely impaired the growth and proliferation (62% inhibition) of rat hepatocytes. AGEs at 100 μg/mL and 50 μg/mL inhibited the growth 48% and 28.8%, respectively, in a concentration dependent manner. While the cells co-incubated with HSA (200 μg/mL) were found normal and proliferated at a significant rate, as they were observed in normal untreated cells (see Table-4).

TABLE 4

Effect of Fructose-derived AGEs on the Proliferation of Rat Hepatocytes.

| AGEs Concentration | Absorbance (Average) | Percentage Inhibition |
|---|---|---|
| 200 μg/mL | 0.65 | 62.4% |
| 100 μg/mL | 0.78 | 48.6% |
| 50 μg/mL | 0.98 | 28.8% |
| HSA 200 μg/mL | 1.11 | 15.6% |

Effect of 6-nitrobenzimidazole derivative (24 μM) on the hepatocytes proliferation, co-incubated with fructose-derived AGEs. Anti-glycation compound 4, belonging to 6-nitrobenzimidazoles class, co-incubated with fructose-derived AGEs (200 μg/mL) at 24 concentration, had showed significant effect on the growth and proliferation of rat hepatocytes (see Table-5).

TABLE 5

Effect of 6-Nitrobenzimidazole Derivative on AGE-mediated-Diminished Growth of the Hepatocytes.

| Compound 4 Conc. | Absorbance (Average) | Percentage Inhibition |
|---|---|---|
| 24 μM | 0.91 | 35.8% |
| 33 μM | 0.93 | 34.3% |
| 49 μM | 1.05 | 22.2% |

Effect of 6-nitrobenzimidazole derivative (33 μM) on the hepatocytes proliferation, co-incubated with fructose-derived AGEs. Compound 4 was also evaluated at 33 μM for its anti-AGE effect on the hepatocytes proliferation. Compound 4 significantly restored the growth and proliferation of the cells, co-incubated with fructose-derived AGEs (200 μg/mL) for 24 hours, in a dose dependent manner (see Table-5).

Effect of 6-nitrobenzimidazole derivative (49 μM) on the hepatocytes proliferation, co-incubated with fructose-derived AGEs. The effect of anti-glycation compound 4 of 6-Nitrobenzimidazole at relatively higher concentration (49 μM) was also studied. Compound 4 was found as effective as 33 μM concentration in reducing the toxicity of AGEs (see Table-5).

Discussion: Compound 4 belongs to 6-nitrobenzimidazole class, was found significantly effective at different concentrations (such as 24, 33 and 49 μM) in ameliorating the AGEs-mediated diminished growth of rat hepatocytes. Our recognized anti-glycation agent, compound 4 inhibits the AGE-induced toxicity at the cellular levels, and hence prevents the tissues from prematureaging.

What is claimed is:

1. A method of inhibiting the formation of advanced glycation end products in diabetes with low cytotoxic effect by administering a group of 6-Nitrobenzimidazole derivatives consisting of 3-(6-Nitro-1H-benzimidazol-2-yl)-1,2-benzenediol; 2-(6-Nitro-1H-benzimidazol-2-yl)-1,4-benzenediol; 6-Nitro-2-(3-thienyl)-1H-benzimidazole; 4-(6-Nitro-1H-benzimidazol-2-yl)-1,2,3-benzenetriol; 2-(6-Nitro-1H-benzimidazol-2-yl)-1,3,5-benzenetriol; 4-(6-Nitro-1H-benzimidazol-2-yl)-1,2-benzenediol; 4-(6-Nitro-1H-benzimidazol-2-yl)-1,3-benzenediol; 2-(4-Methylphenyl)-6-nitro-1H-benzimidazole; 6-Nitro-2-(4-nitrophenyl)-1H-benzimidazole; and 4-(6-Nitro-1H-benzimidazol-2-yl) phenol to a mammal in need thereof.

2. The method of claim 1 wherein the 6-Nitrobenzimidazole derivative is used to reduce the deleterious effects of advanced glycation end products at the post-receptor level.

3. The method of claim 1 wherein the 6-Nitrobenzimidazole derivatives are used to treat a disease associated with advanced glycation end products.

* * * * *